US007214766B2

(12) United States Patent
Everett et al.

(10) Patent No.: US 7,214,766 B2
(45) Date of Patent: May 8, 2007

(54) PEPTIDES WITH ENHANCED STABILITY TO PROTEASE DEGRADATION

(76) Inventors: Nicholas P. Everett, 604 Apple Tree La., Meadow Vista, CA (US) 95722; Qingshun Li, 2268 Cambreling Dr., Lexington, KY (US) 40515; Christopher Lawrence, 625 Sheridan Dr., Lexington, KY (US) 40503; H. Maelor Davies, 2137 Leafland Pl., Lexington, KY (US) 40515

( * ) Notice: Subject to any disclaimer, the term of this patent is extended or adjusted under 35 U.S.C. 154(b) by 563 days.

(21) Appl. No.: 10/252,773

(22) Filed: Sep. 23, 2002

(65) Prior Publication Data

US 2003/0131383 A1    Jul. 10, 2003

Related U.S. Application Data

(62) Division of application No. 09/431,546, filed on Oct. 29, 1999, now abandoned.

(60) Provisional application No. 60/106,573, filed on Nov. 2, 1998, provisional application No. 60/106,373, filed on Oct. 30, 1998.

(51) Int. Cl.
  *C07K 2/00*     (2006.01)
  *C07K 11/00*    (2006.01)
  *C12Q 1/68*     (2006.01)
(52) U.S. Cl. .................. 530/300; 530/327; 514/44; 435/6
(58) Field of Classification Search ............... None
  See application file for complete search history.

(56) References Cited

U.S. PATENT DOCUMENTS

| 5,421,839 | A | 6/1995 | Ulbrich et al. ............... 47/58 |
| 5,424,395 | A | 6/1995 | Bascomb et al. ........... 530/326 |
| 5,519,115 | A | 5/1996 | Mapelli et al. ............. 530/324 |
| 5,773,696 | A | 6/1998 | Liang et al. ................ 800/205 |
| 5,824,869 | A | 10/1998 | Broekaert et al. ......... 800/205 |
| 5,850,025 | A | 12/1998 | Mirkov et al. .............. 800/279 |
| 6,015,941 | A | 1/2000 | Rao ........................... 800/279 |
| 6,538,106 | B1 * | 3/2003 | Fraser et al. ............... 530/327 |

FOREIGN PATENT DOCUMENTS

WO    WO 98/07745    *    2/1998

OTHER PUBLICATIONS

Iwahori et al., *Synthesis of Reversed Magainin 2 Analogs Enhanced Antibacterial Activity*, Biol. Pharm. Bull. 20(3):267-270 (1997).
Selsted et al., *Indolicidin, a Novel Bactericidal Tridecapeptide Amide from Neutrophils*, J. Biol. Chem. 267(7):4292-4295 (1992).
Subbalakshmi et al., *Requirements for Antibacterial and Hemolytic Activities in the Bovine Neutrophil Derived 13-residue Peptide Indolicidin*, FEBS Letters 395:48-52 (1996).
Subbalakshmi et al., *Interaction of Indolicidin, a 13-Residue Rich in Tryptophan and Proline and its Analogues with Model Membranes*, J. Biosci. 23(1):9-13 (1998).
Van Abel et al., *Synthesis and Characterization of Indolicidin, a Tryptophan-rich Antimicrobial Peptide from Bovine Neutrophils*, Int. J. Peptide Protein Res. 45:401-409 (1995).
Ladokhin et al., *Bilayer Interactions of Indolicidin, a Small Antimicrobial Peptide Rich in Tryptophan, Proline, and Basic Amino Acids*, Biophysical Journal 72:794-805 (1997).
Owens et al., *A Single Amino Acid Substitution in the Antimicrobial Defense Protein Cecropin B is Associated with Diminished Degradation by Leaf Intercellular Fluid*, MPMI 10(4):525-528 (1997).
Jaynes et al., *Increasing Bacterial Disease Resistance in Plants Utilizing Antibacterial Genes from Insects*, BioEssays 6(6):263-270 (1987).
Lim et al., *Synthesis and Bioligical Characterization of Indolicidin Analogues*, J. Biochem. Mol. Biol. 30(3):229-233 (1997).
Merrifield et al., *Retro and Retroenantio Analogs of Cecropin-Melittin Hybrids* Proc. Natl. Acad. Sci. USA 92:3449-3453 (1995).
Mills et al. *Evidence of the Breakdown of Cecropin B by Proteinases in the Intercellular Fluid of Peach Leaves*, Plant Sci. 104:17-22 (1994).
Robinson, Jr. et al., *Anti-HIV-1 Activity of Indolicidin, an Antimicrobial Peptide from Neutrophils*, J. Leukocyte Biol. 63:94-100 (1998).
Everett, N.P., *Design of Antifungal Peptides for Agricultural Applications*, Chapter 20, pp. 279-291 (1994).
Allefs et al., *Erwina Soft Rot Resistance of Potato Cultivars Transformed with a Gene Construct Coding for Antimicrobial Peptide Cecropin B is not Altered*, Am. Potato J. 72:437-445 (1995).
Falla et al., *Mode of Action of the Antimicrobial Peptide Indolicidin*, J. Bio. Chem. 271(32):19298-19303 (1994).
Falla et al., *Improved Activity of a Synthetic Indolicidin Analog*, Antimicrobial Agents and Chemotherapy 41(4):771-775 (1997).
Florack et al., *Expression of Giant Silkmoth Cecropin B Genes in Tobacco*, Transgenic Research 4:132-141 (1995).
Hancock, E.W. and Lehrer, R., *Cationic Peptides: A New Source of Antibiotics*, Tibtech 16:82-88 (1998).
Piers et al., *Recombinant DNA Procedures for Producing Small Antimicrobial Cationic Peptides in Bacteria*, Gene 134:7-13 (1993).
Enfors, S., *Control of in vivo Proteolysis in the Production of Recombinant Proteins*, Tibtech 10:310-315 (1992).

(Continued)

*Primary Examiner*—Sean McGarry
(74) *Attorney, Agent, or Firm*—Womble Carlyle Sandridge & Rice, PLLC

(57) ABSTRACT

Disclosed are peptides that have enhanced stability against plant proteases and are useful in the control of plant diseases. The peptides also have the ability to protect other peptides, polypeptides or proteins from degradation by proteases of plant, fungal, viral, bacterial, insect or other origin. DNA encoding the peptides of the present invention can be co-expressed with other DNA encoding exogenous peptides in transgenic plants as a method for protecting foreign peptides from degradation by proteases. Also disclosed are nucleic acid sequences, microorganisms, plants, and compositions useful for the treatment of plant diseases.

3 Claims, 3 Drawing Sheets

OTHER PUBLICATIONS

Helmerhorst et al., *A Critical Comparision of the Hemolytic and Fungal Activities of Cationic Antimicrobial Peptides*, FEBS Letters 449:105-116 (1999).

Peschel et al., *Inactivation of the dlt Operon in Staphylococcus aureus Confers Sensitivity to Defensins, Protegrins, and Other Antimicrobial Peptides*, J. Bio. Chem. 274(13):8405-8410 (1999).

Rao, A.G., *Antimicrobial Peptides*, MPMI 8(1):6-13 (1995).

Broekaert et al., Antimicrobial Peptides from Plants, Critical Reviews in Plant Sciences 16(3):297-323 (1997).

Mourgues et al., *Strategies to Improve Plant Resistance to Bacterial Diseases Through Genetic Engineering*, Tibtech 16:203-210 (1998).

Mourgues et al., *Activity of Different Antibacterial Peptides on Erwinia amylovora Growth, and Evaluation of the Phytotoxicity and Stability of Cecropins*, Plant Sci. 139:83-91 (1998).

De Bolle et al., *Antimicrobial Peptides from Mirabilis jalapa and Amaranthus caudatus: Expression, Processing, Localization and Biological Activity in Transgenic Tobacco*, Plant Mol. Bio. 31:993-1008 (1996).

Cavallarin et al., *Cecropin A-Derived Peptides are Potent Inhibitors of Fungal Plant Pathogens*, MPMI 11(3):218-227 (1998).

Powell et al., *Synthetic Antimicrobial Peptide Design*, MPMI 8(5):792-794 (1995).

Chrispeels, M.J., *Sorting of Proteins in the Secretory System*, Annu. Rev. Plant. Physiol. Plant Mol. Biol. 42:21-53 (1991).

P. Staubitz et al., Journal Of Peptide Science, 7:552-564 (2001).

Merrifield, et al., Proc. Natl. Acad. Sci. 92:3449-3453 (1995).

Ido, et al., Science 277:563-566 (1997).

Pinilla, et al., J. Mol. Biol. 283:1013-1025 (1998).

Vunnam, et al., J. Peptide Res. 51:38-44 (1998).

Zanetti, et al., FEBS 374:1-5 (1995).

Nagpal, et al., J. Biol. Chem. 274(33):23296-23304 (1999).

Gao, et al., J. Clin. Inv. 106(3):439-448 (2000).

* cited by examiner

FIG. 1

RIL gene constructs

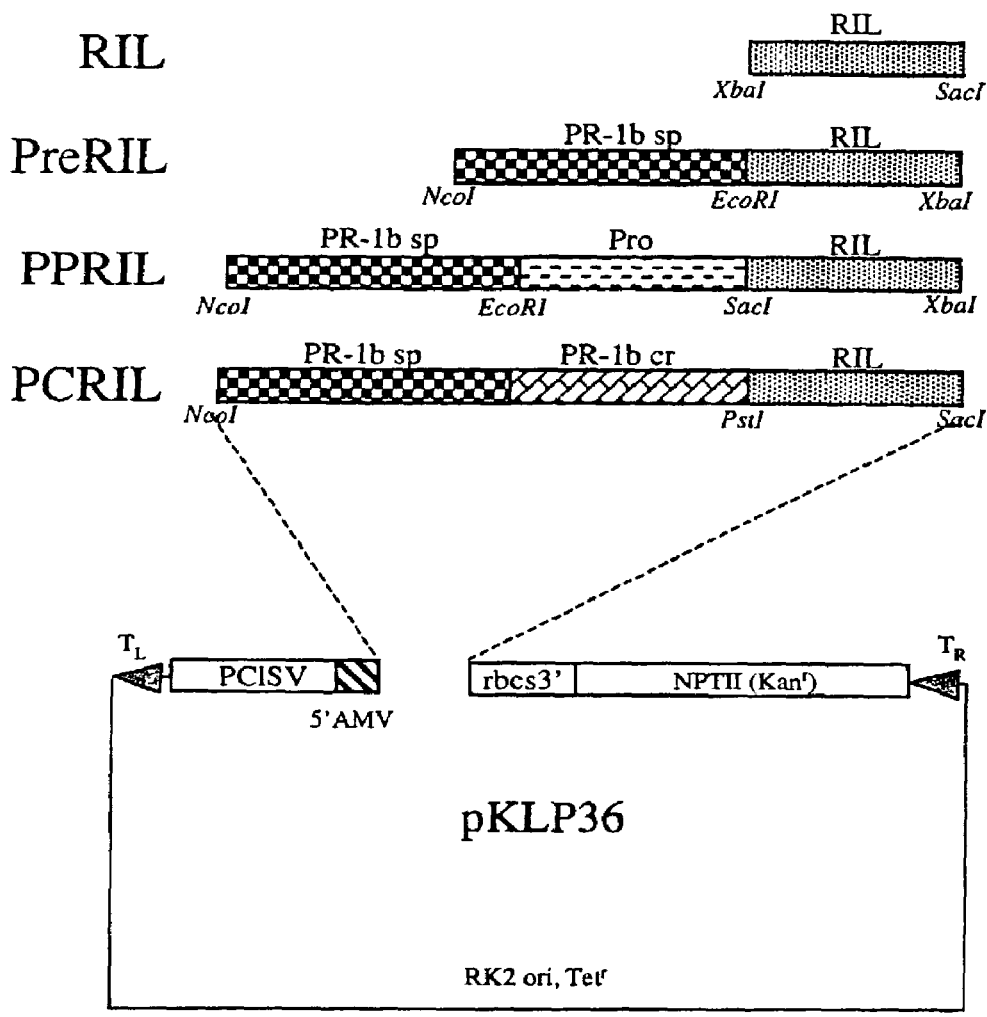

Abreations:
RIL: reverse indolicidin; PR-1b sp, Pathogen related protein 1b signal peptide; PR-1b cr, PR-1b coding region; Pro, the modified pro sequence of Magainin; PCISV, duplicated promoter from peanut chlorotic streak caulimovirus; 5' AMV, the leader sequence of alfalfa mosaic virus; rbcs3', 3' untranslated region of rubisco small subunit gene; NPTII, the gene confer Kanamycin resistance in plant; $T_L$ and $T_R$, the T-DNA left and right border, respectively; Kan$^r$ and Tet$^r$, Kanamycine and tetracycline resistance gene, respectively; ori, the origin for DNA replication.

| Lines | % surving plants |
|---|---|
| KYLX | 0.16 |
| RIL 26 | 0 48 |
| PCRIL 24 | 0.36 |
| PCRIL 26 | 0.61 |

Fig 3. *Erwinia carotovara* resistance tests of Rev4 tobacco transgenic plants. Two µl of a bacterial suspension were inoculated onto the leaf of each tobacco seedling (4 weeks old), cultured in 24-well plates containing MS medium. 8 replications of 6 plants for each transgenic line and controls were tested.

PEPTIDES WITH ENHANCED STABILITY TO PROTEASE DEGRADATION

CROSS-REFERENCE TO RELATED APPLICATIONS

The present application is a divisional of U.S. patent application Ser. No. 09/431,546, filed Oct. 29, 1999, now abandoned which claims the benefit of U.S. Provisional Patent Application Nos. 60/106,373 and 60/106,573, filed Oct. 30, 1998 and Nov. 2, 1998, respectively, the disclosures of which are hereby incorporated by reference herein.

BACKGROUND OF THE INVENTION

The present invention relates to antimicrobial peptides which are resistant to proteases and which have the ability to reduce the extent of protease degradation of peptides, polypeptides and proteins in plants.

Antimicrobial peptides are produced by a wide range of organisms as part of their defense against infection. See Hancock & Lehrer, 1998, TIBTECH, 16:82–88; Everett, 1994, Chpt. 20 In: Natural and Engineered Pest Management Agents, eds. Hedin, Menn & Hollingworth, ACS Symposium Series 551, pp. 278–91. Examples of such peptides include cecropins, attacins and diptericins which are involved in cell-free immunity in insects, the apidaecins from honeybees, the defensins from mammalian phagocytes, and the magainins from frog skin. Plants also produce certain classes of antimicrobial peptides which are thought to play a role in resistance to microbial plant pathogens. See Broekaert et al., 1997, Critical Reviews in Plant Sciences, 16:297–323.

Plants have been genetically engineered to produce antimicrobial peptides, both natural and synthetic to increase resistance to disease. See Jaynes et al., 1987, BioEssays, 6:263-70; Hancock and Lehrer, 1998, TIBTECH, 16:82–88. Unfortunately, this approach has met with very limited success. Either the amount of peptide produced by the transgenic plant is too small and/or the plants are no less Lehrer, 1998, TIBTECH, 16:82–88. A major limitation to the expression of foreign peptides in transgenic plants is due to the susceptibility of the foreign peptides to rapid degradation by proteases. For example, transgenic potato cultivars which express a gene encoding the antimicrobial peptide cecropin B at levels up to 0.6% of total mRNA produce no detectable cecropin B peptide and no improvement in resistance to potato soft rot. See Sjefke et al., 1995, American Potato Journal, 72:437–45. Similar studies in tobacco have demonstrated that expression of cecropin B genes also does not result in detectable cecropin B peptide levels and resistance to bacterial infections. See Florack et al., 1995, Transgenic Research 4:132–41. Studies have also shown that cecropin B and antimicrobial peptides related to magainins are rapidly degraded by proteases in the intercellular fluid of plant leaves. See Mills et al., 1994, Plant Science, 104:17–22 and Everett, 1994, Chpt. 20 In: Natural and Engineered Pest Management Agents, eds. Hedin, Menn & Hollingworth, ACS Symposium Series 551, pp. 278–91.

One proposed solution to the problem of peptide instability due to protease degradation has been to identify the protease-sensitive sites within a particular peptide and to design amino acid substitutions that increase the stability of peptides to plant proteases while retaining the antimicrobial activity of the peptides. This approach resulted in a synthetic magainin derivative having the amino acid sequence Met-Gly-Ile-Gly-Lys-Phe-Leu-Arg-Glu-Ala-Gly-Lys-Phe-Gly-Lys-Ala-Phe-Val-Gly-Glu-Ile-Met-Lys-Pro (SEQ ID NO:1) that had enhanced stability against proteases found in the intercellular fluid of plant tissues and was therefore an improved candidate for use in or on plants. See Everett, 1994, Chpt. 20 In: Natural and Engineered Pest Management Agents, eds. Hedin, Menn & Hollingworth, ACS Symposium Series 551, pp. 278–91; U.S. Pat. Nos. 5,424, 395 and 5,519,115.

Another proposed solution to the problem of peptide instability has been to produce the reverse- or retro-analogs of natural antimicrobial peptides or their synthetic derivatives. See U.S. Pat. No. 5,519,115, and Merrifield et al., 1995, PNAS, 92:3449–53. Such reverse-peptides retain the same general three-dimensional structure (e.g., alpha-helix) as the parent peptide except for the conformation around internal protease-sensitive sites and the characteristics of the N- and C-termini. Reverse peptides are purported not only to retain the biological activity of the non-reversed "normal" peptide but may possess enhanced properties, including increased antibacterial activity and reduced hemolysis. See Iwahori et al., 1997, Biol. Pharm. Bull. 20:267–70.

Indolicidin, having the amino acid sequence Ile-Leu-Pro-Trp-Lys-Trp-Pro-Trp-Trp-Pro-Trp-Arg-Arg, (SEQ ID NO:2) is a potent antimicrobial tridecapeptide. It was originally purified from cytoplasmic granules of bovine neutrophils. See Selsted et al., 1993, J. Biol. Chem., 267:4292–95. It is a member of a class of proline-rich peptides that have been recovered from the leukocytes of different mammals, a marine invertebrate and insect haemolymph. See Hancock and Lehrer, 1998, TIBTECH, 16:82–88. The antimicrobial potencies of natural and synthetic indolicidin are identical. See Van Abel et al., 1995, Int. J. Protein Res. 45:401–09. The mode of antibacterial action of indolicidin has been reported to be based on the disruption of the cytoplasmic membrane by channel formation. See Falla et al., 1996, J. Biol. Chem. 32:19298–303. More recently, it has been suggested that membrane permeabilization is likely to occur due to deformation of the membrane surface rather than formation of transmembrane channels by indolicidin and its analogs. See Subbalakshmi et al., 1998, J. Biosci., 23:9–13.

Numerous analogs of indolicidin have been synthesized and tested in attempts to evaluate the requirements for antimicrobial and hemolytic activities, and to increase activity. Subbalakshmi et al. (FEBS Letters 395:48–52 (1996)) reports that peptides in which proline was replaced by alanine and tryptophan was replaced by phenylalanine exhibit antibacterial activities comparable to that of indolicidin. The replacement of tryptophan by phenylalanine, however resulted in a loss of hemolytic activity. Falla and Hancock (Antimicrobial Agents and Chemotherapy, 41:771–75 (1997)) tested a synthetic peptide, CP-11, Ile-Leu-Lys-Lys-Trp-Pro-Trp-Trp-Pro-Trp-Arg-Arg, (SEQ ID NO:3) based on indolicidin, which was designed to increase the number of positively charged residues, maintain the short length (13 amino acids), and enhance the amphipathicity relative to indolicidin. They found that CP-11 had better activity against *E. coli, Pseudomonas aeruginosa*, and *Candida albicans*, but reduced activity against *Staphylococcus aureus*. Lim et al. (J. Biochem. Mol. Biol. 30:229–33 (1997)) tested the effects of substituting certain tryptophan, proline or arginine residues in indolicidin. Substitutions of some tryptophan residues by isoleucine or glycine were tolerated but substitution of Pro$^7$ with alanine significantly reduced activity against *E. coli*. Substitutions of either Arg$^{12}$ or Arg$^{13}$ with alanine also reduced biological activity.

SUMMARY OF THE INVENTION

Applicants have discovered that indolicidin exhibits remarkable resistance to proteolysis by proteases. Applicants have also discovered that Rev4, the reverse peptide of indolicidin, and derivatives and analogs of indolicidin and Rev4 share these properties while maintaining antimicrobial properties. Applicants have further discovered that exogenous or non-native peptides, polypeptides and proteins of agronomic interest (hereinafter "proteins of agronomic interest") exhibit greater resistance to degradation by multiple classes of proteases that have different active sites and substrate specificities in the presence of indolicidin, Rev4 and related structures.

One aspect of the present invention is directed to an isolated and purified peptide which is, includes, or consists essentially of Rev4, or a functional equivalent thereof that exhibits antimicrobial properties and/or renders other proteins applied to and/or produced by plants more resistant to proteolytic degradation. This aspect of the present invention also entails nucleic acids including or consisting essentially of sequences encoding Rev4, and nucleic acid constructs such as vectors containing the Rev4-encoding sequence. Recombinant cells such as plants and bacteria (e.g., *Agrobacterium tumefaciens*) and protoplast containing the Rev4-encoding sequence are also entailed. Transgenic plants that express Rev4-encoding nucleic acids exhibit increased resistance to microbial pathogens that infect plants. Transgenic plants can be made in accordance with standard techniques including regenerating plants from transformed protoplasts or transformed plant tissue. Yet another embodiment of this aspect of the invention relates to seeds derived from the transgenic plants. In yet another embodiment, increased resistance to microbial infection may be imparted to a given plant species by applying to the plant a composition containing the Rev4 protein or functional equivalent thereof. These compositions may be in the form of a dry powder or a liquid dispersion suitable for spraying, etc.

Another aspect of the present invention is directed to a method of decreasing the extent of or inhibiting proteolytic degradation of a non-native protein susceptible to proteolytic degradation, on or in a plant. The method entails administering to a plant indolicidin, Rev4 or a functional equivalent thereof, before simultaneously with, or after the administration of a non-native protein of interest, such as an anti-pathogenic protein. The "administration" of the Rev4 or indolicidin as in the case of the Rev4-containing compositions, above, may be accomplished by direct application to the plant or by genetic engineering techniques whereby a transgenic plant is produced. In the case of transgenics, the non-native construct containing the Rev4 or indolicidin may be constructed so as to be expressed before, during or suitably after expression of the non-native DNA encoding the non-native protein of interest. This method may also be described in terms of a method of preserving or increasing the activity of a given non-native protein applied to or produced by a plant, the non-native protein being susceptible to proteolytic degradation. In preferred embodiments, transgenic plants contain recombinant nucleic acid molecules containing a first sequence encoding Rev4, indolicidin, or a functional equivalent thereof, and a second sequence encoding the protein of interest.

One aspect of the present invention is directed to synthetic peptides comprising Rev4 having the amino acid sequence Arg-Arg-Trp-Pro-Trp-Trp-Pro-Trp-Lys-Trp-Pro-Leu-Ile ("Rev4"), and analogs and derivatives of Rev4 that exhibit antimicrobial and anti-proteolytic properties, nucleic acids encoding these peptides, as well as nucleic acid constructs, vectors and hosts containing the nucleic acids are also disclosed.

Another aspect of the present invention provides a method for increasing resistance of peptides, polypeptides and proteins of agronomic interest to degradation or inactivation by proteases or reducing the extent of protease degradation. In preferred embodiments, DNAs encoding the peptides of the present invention are co-expressed with another non-native nucleic acid encoding an antifungal, antibacterial, antiviral and insecticidal protein, or any other preferred proteins of interest that are beneficial to the plant and/or impart resistance to plant disease and pathogens.

The present invention also provides nucleic acids and genetic constructs comprising sequences that encode Rev4 and biologically functional equivalents thereof, and methods for inserting such nucleic acid sequences and genetic constructs into host cells for the production of the peptides encoded thereby.

Transgenic plants, parts or cells thereof, and seeds derived from the plants are also included.

The present invention also provides recombinant microorganisms and protoplasts containing nucleic acid sequences that encode the peptides according to the present invention.

The present invention also provides antipathogenic compositions, comprising at least one of the peptides of the present invention along with at least one antifungal, antibacterial, antiviral or insecticidal agent.

The compositions of the present invention also include recombinant host cells, such as bacterial (e.g., *Agrobacterium tumefaciens*) and fungal cells, which produce the peptides of the present invention and at least one antipathogenic protein. In preferred embodiments, the compositions are applied to roots and/or leaves. The cells colonize the roots and/or leaves of plants.

BRIEF DESCRIPTION OF THE DRAWINGS

FIG. 1 is gene construct RIL which includes a nucleic acid sequence encoding Rev4 (wherein RIL: reverse indolicidin; PR-1b sp, Pathogen related protein 1b signal peptide; PR-1b cr, PR-1b coding region; Pro, the modified pro sequence of Magainin; PCISV, duplicated promoter from peanut chlorotic streak caulimovirus; 5'AMV, the leader sequence of alfalfa mosaic virus; rbcs3', 3' untranslated region of rubisco small subunit gene; NPTII, the gene confer Kanamycin resistance in plant; $T_L$ and $T_R$, the T-DNA left and right border, respectively; $Kan^r$ and $Tet^r$, Kanamycine and tetracycline resistance gene, respectively; ori, the origin for DNA replication).

DETAILED DESCRIPTION

Figure 2:
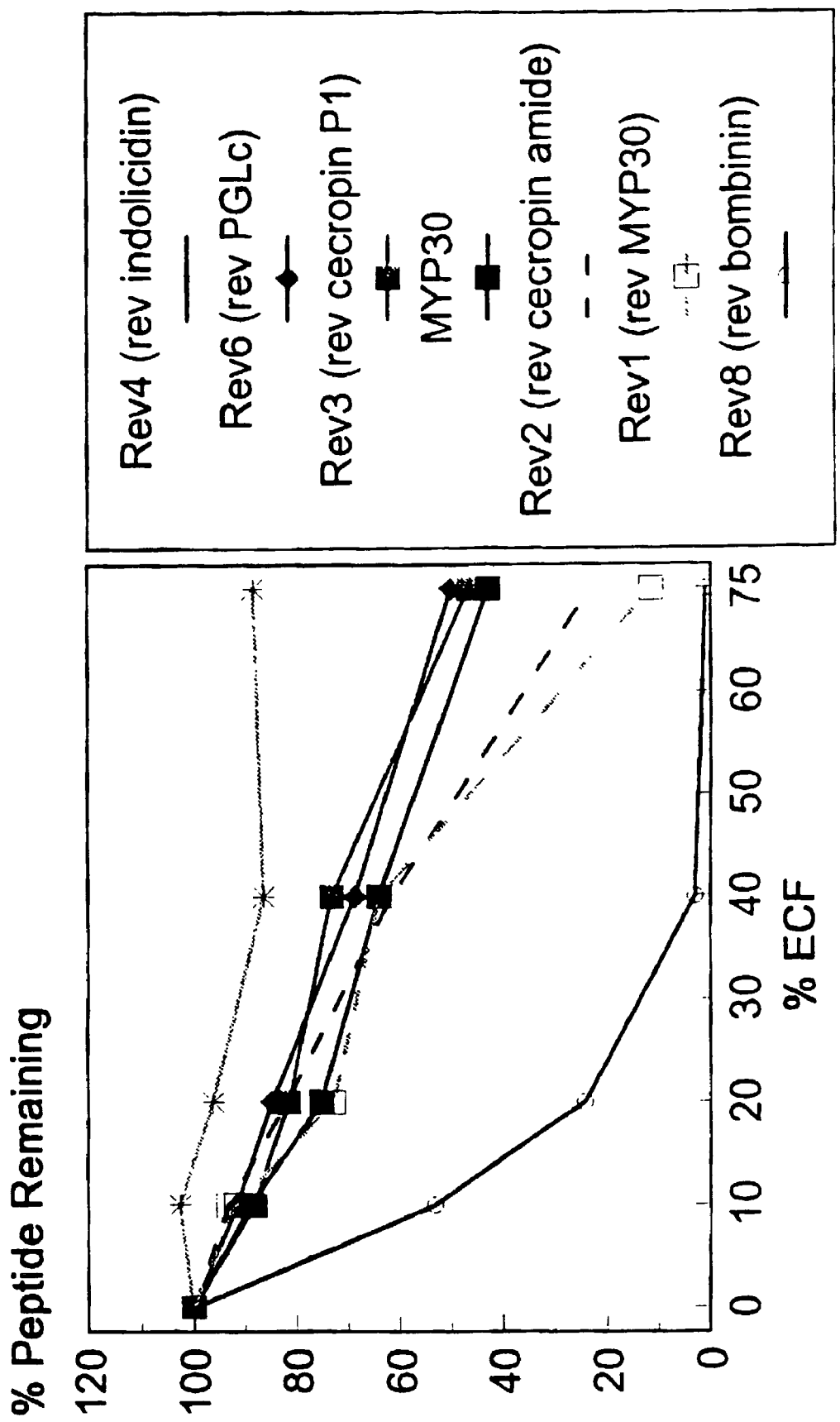
FIG. 2 is graph depicting the stability of Rev4 and related structures to proteolysis.
Figure 3:
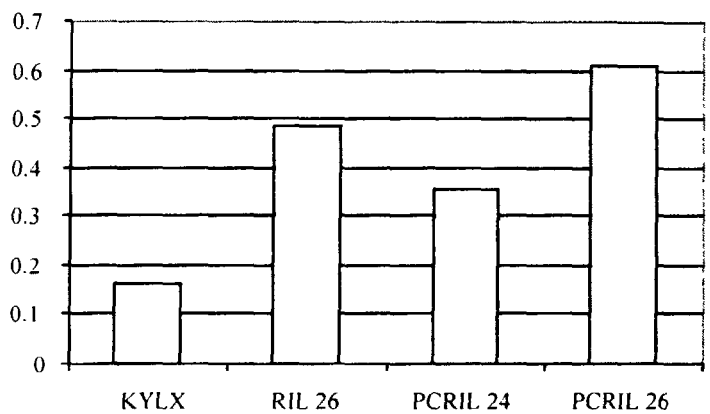
FIG. 3 is a bar graph depicting bacterial pathogen *Erwinia carotovara* resistance of transgenic plants containing Rev4.

The contents of each of the publications discussed in this specification, including the references cited therein, are herein incorporated by reference in their entirety.

The phrase "functional equivalent peptide" is meant to include peptide, polypeptide, and protein derivatives and analogs of indolicidin and Rev4 that exhibit sequence similarity to indolicidin and Rev4, and which exhibit the same or similar antimicrobial activity and/or ability to increase the resistance of other proteins to degradation or inactivation by proteases. These properties may be determined by the methods described in Examples 7–13 of the specification.

Functional equivalent peptides also include amino acid sequences containing conservative amino acid changes in the sequence. In such amino acid sequences, one or more amino acids in the fundamental sequence is substituted with another amino acid or amino acids, the charge and polarity of which is similar to that of the native amino acid, i.e., a conservative amino acid substitution resulting in a silent change. The amino acids may include any of the D-amino acids corresponding to the 20 L-amino acids commonly found in proteins, imino amino acids, rare amino acids, such as hydroxylysine, or non-protein amino acids, such as homserine and ornithine. A peptide may have none, one, or more of these derivatives and D-amino acids.

Substitutions, additions, deletions and non-naturally occurring derivatives of amino acid residues are also within the scope of functional equivalent peptides of present invention.

Amino acid substitutions within the fundamental polypeptide sequences are preferably selected from other members of the class to which the naturally occurring amino acid belongs. See Table 1. Amino acids are typically divided into the following four groups: (1) acidic amino acids; (2) basic amino acids; (3) neutral polar amino acids; and (4) neutral non-polar amino acids. Conservative amino acid changes within the fundamental polypeptide sequence are made by substituting one amino acid within the same group.

TABLE 1

PREFERRED AMINO ACID SUBSTITUTIONS

| Arg | Trp | Pro | Lys | Leu | Ile |
|-----|-----|-----|-----|-----|-----|
| Lys | Gly | Trp | Arg | Pro | Pro |
| His | Ala | Glu | His | Trp | Trp |
|     | Val | Ala |     | Gly | Gly |
|     | Leu | Val |     | Ala | Ala |
|     | Ile | Leu |     | Val | Val |
|     | Pro | Ile |     | Ile | Leu |
|     | Phe | Phe |     | Phe | Phe |
|     | Met | Met |     | Met | Met |
|     | Lys | Lys |     | Lys | Lys |

Preferred equivalents of indolicidin and Rev4 are represented by the following sequences:

| (1) | Y-Y-Y-Y-X-Y-Y-Y-Y-Y-X-X |
| (2) | X-X-Y-Y-Y-Y-Y-X-Y-Y-Y   |

In other preferred embodiments, the functional equivalent proteins contemplated herein possess about 70% or greater sequence similarity, more preferably about 80% or greater sequence similarity, and most preferably about 90% or greater sequence similarity.

The modification of any of the peptide residues in the sequence, including the N- or C-terminal residues, is also within the scope of this invention. The peptides may be altered by chemical or biological means, such as, for example, methylation and amidation, and alteration of amino acid sides chain, such as acylation. The peptides may also be labeled, such as with a radioactive label, a fluorescent label, a mass spectrometry tag, biotin and the like. The peptides may also include additions of amino acids to the N- and C-termini. For example, a glycine residue may be added to the C-terminus to provide a precursor for C-terminal amidation. See Bradbury, A. F. and Smyth, D. G., 1991, TIBS 16:112.

The peptides may also be conjugated, fused, or crosslinked to the protein of interest. Examples include Ser-Rev4-OH comprising the amino acid sequence Ser-Arg-Arg-Trp-Pro-Trp-Trp-Pro-Trp-Lys-Trp-Pro-Leu-Ile (SEQ ID NO:5) and Rev4-C-fusion comprising the amino acid sequence Arg-Arg-Trp-Pro-Trp-Trp-=Pro-Trp-Lys-Trp-Pro-Leu-Ile-Gly-Gly-Gly-Tyr-Asp-Pro-Ala-Pro-Pro-Pro-Pro-Pro-Pro (SEQ ID NO:6).

The peptides of the present invention may be synthesized in accordance with standard techniques, including, but not limited to, chemical synthesis, synthesis by automated procedure, synthesis in heterologous biological systems such as microbial, plant and animal systems, tissue cultures, cell cultures, or in vitro translation systems. For example, the peptides may be synthesized using standard solid-phase Fmoc protection strategy with HATU as the coupling agent. Other synthesis techniques include the t-Boc protection strategy and the use of different coupling reagents.

The present invention also includes nucleic acid sequences comprising or consisting essentially of sequences that encode peptides of the present invention. Nucleic acid sequences include DNA, RNA, genomic DNA, mitochondrial DNA, chloroplast DNA, plasmid DNA, cDNA, synthetic DNA, and mRNA nucleotide sequences.

The present invention also comprises nucleic acid constructs comprising the nucleic acids of the present invention and methods for inserting such nucleic acids into host cells. Preferably, the nucleic acid constructs contain a promoter sequence and a sequence encoding Rev4 or a functional equivalent thereof. The nucleic acid sequences can be inserted into a variety of host systems suitable for production of the peptide, including, for example, microorganisms, fungi and plants. Examples of promoters suitable for use in the present invention include broad expression promoters such as CaMV and Brassica ALS3, tissue/cell-type specific promoters such as the maize ZRP2; pathogen induced promoters such as HMG2 and tobacco hsr203J; pest/wound inducible promoters such as potato pin II, potato wun 1, and poplar Win6; stress inducible promoters such as *Arabidopsis* rd29A and *Arabidopsis* adh; and chemically induced promoters such as wheat Em, soybean GH3, and potato CDI.

Other regulatory sequences may also be included in the construct. Such sequences include, without limitation, an enhancer, repressor, ribosome binding site, transcription termination signal sequence, secretion signal sequence, origin of replication, selectable marker, and the like. The regulatory sequences are operationally associated with one another to allow transcription and subsequent translation.

Reporter genes may also be included in the construct in order to monitor transcription and translation. In preferred embodiments, the nucleic acid sequence encoding Rev4 or a functional equivalent is introduced into a plant using an expression vector. Many expression vectors have been developed for the production of recombinant plants, including bacteria, plasmids and viruses. Plant viral vectors suitable for the present invention include, for example, those disclosed in U.S. Pat. No. 5,316,931. The proteins and nucleic acids of the present invention are administered to a plant. Transgenic plants expressing Rev4 exhibit resistance to infection by microbial plant pathogens.

In another embodiment, transgenic plants produce both indolicidin or Rev4 and another non-native protein. The transgenic plants are produced by preparing a plant having a genome that contains the DNA sequence encoding indolicidin, Rev4 or functional equivalents thereof which are expressed. Preferably the transgenic plant is prepared by stably transforming a protoplast with the DNA sequence encoding indolicidin, Rev4 or functional equivalents thereof. The transgenic plant may also be prepared by introducing and regenerating the plant from plant tissue containing the DNA molecule.

Preferably, the peptides of the present invention are co-expressed with antibacterial, antifungal, antiviral and/or insecticidal proteins, proteins of agronomic interest include proteins derived from *Bacillus thuringiensis* (B.t.), other *Bacillus* species, or *Photorhabdus* or *Xenorhabdus* species; proteins involved in improving the quality of plant products or agronomic performance of plants, as well as peptides or proteins that are to be produced in plants for the purpose of extraction and use as pharmaceutical products, agricultural products, feed or food additives, industrial enzymes; peptides or proteins that cause an alteration in plant metabolism that leads to the production of metabolites that can be extracted and used as pharmaceutical products, feed and food additives, agricultural products such as fungicides or insecticides, and specialty chemicals or chemical intermediates that have commercial value.

In more preferred embodiments, the transgenic plants co-produce indolicidin or Rev4 and Magainins, reverse Magainins, PGLc, reverse PGLc, PI's, reverse PI's, Cecropins, reverse Cecropins, Sarcotoxins, reverse Sarcotoxins, Bombinins, reverse Bombinins, XPFs, reverse XPF's, Thionins, reverse Thionins, Defensins, reverse Defensins, Melittins, reverse Melittins, PGLa, and reverse PGLa, Dermaseptins, reverse Dermaseptins, Histatins, reverse Histatins, peptides derived from pig myeloid cells, peptides derived from human neutrophil cathepsin G, antimicrobial peptides from bovine neutrophils, Seminalplasmin, antimicrobial derived from Lactoferrin, Drosocin, Tachyplesins, reverse Tachyplesins, Maize Basic Peptide I, Tracheal antimicrobial peptides, Antimicrobial peptides from seeds of amaranth, antimicrobial peptides from seeds of *Mirabilis jalapa*, Ranalexin, Brevenin, Subtilin, Nisin, Epidermin, Lactacin 481, and basic amphipathic peptides.

The co-production of a peptide that can protect a second protein from degradation or inactivation by proteases found in or on plants is advantageous in many different situations. For example, if the second protein has antifungal, antibacterial, antiviral or insecticidal activity, but is susceptible to degradation or inactivation by plant proteases, the present invention enables the use of multiple antimicrobial proteins that exploit more than one mode of action to protect plants against disease caused by pathogens. This co-production thus reduces the possibility of developing resistant strains of pathogens, broaden the scope of plant disease resistance, and results in synergistic control of plant pathogens. If the second peptide, polypeptide or protein is susceptible to degradation or inactivation by proteases endogenous to an invading plant pathogen, the use of the present invention may increase the range of pathogens against which a particular anti-pathogenic protein is active. Thus, because of the remarkable stability of the peptides to degradation or inactivation by the complex mixture of proteases present in whole cell extracts of plant tissues, the present invention may be particularly useful in maintaining antimicrobial activity in plant tissues that have been damaged by insects or post-harvest handling.

Similarly, potentially labile proteins may be protected from undue protease degradation or inactivation during extraction from plant tissues. If the second protein is insecticidal, the present invention provides a mechanism by which the insecticidal protein is stabilized against plant proteases and that it accumulates to higher concentrations in healthy plant tissues and survive additional proteases, of plant or insect origin, encountered during insect feeding. For protection of feed, food and other products from spoilage caused by insects or microorganisms, the indolicidin and Rev4 peptides do not have to be produced by a plant part that is a component of the feed, food or other product. The peptide may be added during post-harvesting processing and formulation.

Plants suitable for expression or application of the peptides disclosed in the present invention include flowering plants, and preferably, crop plants, e.g., moncots and dicots. More preferred plants include maize, tomato, turfgrass, asparagus, papaya, sunflower, rye, beans, ginger, lotus, bamboo, potato, rice, peanut, barley, malt, wheat, alfalfa, soybean, oat, eggplant, squash, onion, broccoli, sugarcane, sugar beet, beets, apples, oranges, grapefruit, pear, plum, peach, pineapple, grape, rose, carnation, daisy, tulip, Douglas fir, cedar, white pine, scotch pine, spruce, peas, cotton, flax, coffee and tobacco.

The present invention also encompasses the use of nucleic acid sequences or constructs encoding indolicidin or Rev4 to produce recombinant vectors, for example, plasmids, recombinant microorganisms, probes, and primers useful in identifying related nucleic acid sequences that encode peptides that confer resistance to plant disease and which confer stability to peptides, polypeptides, and proteins. The peptides may be synthesized by recombinant production using various host systems, including bacteria, yeast, insect, and mammalian cells.

The present invention also provides antipathogenic compositions comprising indolicidin or Rev4 along with at least one other antifungal, antibacterial, antiviral or insecticidal protein. The compositions can be formulated by conventional methods using any suitable carrier. Other ingredients such as inert materials, surfactants, solvents, and other additives, which are well known in the art, may be added to the compositions. The compositions may also be combined with fertilizers, insecticides, antifungal agents, attractants, sterilizing agents, acaricides, nematodes, and herbicides.

Preferably, the indolicidin or Rev4 is applied in a concentration in the range from about 1 µg/ml to about 50 µg/ml to obtain antimicrobial activity and in a concentration in the range of from about 1 µg/ml to about 100 µg/ml to protect other peptides, polypeptides, and proteins from protease degradation.

The compositions of the present invention also include those in the form of recombinant host cells, such as bacterial and fungal cells, that produce indolicidin or Rev4 and colonize roots and/or leaves of plants. The protease-inhibiting peptides of this invention can be used in various combinations with each other to obtain synergistic activity and/or to provide broader protection against multiple classes of proteases having different active sites and substrate specificity. For example, Rev4 may be combined with another peptide from the indolicidin/Rev4 family of protease-inhibiting peptide which exhibits increased activity in protecting a particular class of peptide, polypeptide or protein or which exhibits increased activity against a particular protease.

The detailed description of the invention has been provided to aid those skilled in the art in practicing the present invention. The detailed description should not be construed to unduly limit the present invention as modifications and variations in the embodiments discussed herein may be made by those of ordinary skill in the art without departing from the scope of the present discovery. The present invention can be better understood from the following illustrative, non-limiting examples.

EXAMPLE 1

Chemical Synthesis and Purification of Rev4 (Amide)

Peptides of the type described in this invention can be synthesized and purified by standard techniques as discussed in detail in U.S. Pat. Nos. 5,424,395 and 5,519,115. For convenience, they may also be purchased from one of many companies that offer custom peptide synthesis. One such company is Genosys Biotechnologies, Inc., P.O. Box 41027, Houston, Tex. 77240 (Tel: 281–363–3693). Synthesis of the C-terminal amide form of Rev4 peptide (Arg Arg Trp Pro Trp Trp Pro Trp Lys Trp Pro Leu Ile) (SEQ ID NO:4)was contracted with Genosys Biotechnologies Inc. HPLC analysis using a VYDAC reverse phase C8 column eluted with a 10–90% gradient of acetonitrile over 34 minutes at a flow rate of 1.5 ml per minute showed the peptide to be greater than 95% pure with a single peak eluting after 24.548 minutes.

EXAMPLE 2

Chemical Synthesis and Purification of Indolicidin

Synthesis of the C-terminal amide form of indolicidin (Ile Leu Pro Trp Lys Trp Pro Trp Trp Pro Trp Arg Arg) (SEQ ID NO:2) was contracted with Genosys Biotechnologies Inc. HPLC analysis using a VYDAC reverse phase C8 column eluted with a 10–90% gradient of acetonitrile over 34 minutes at a flow rate of 1.5 ml per minute showed the peptide to be greater than 95% pure with a single peak eluting after 23.232 minutes.

EXAMPLE 3

Chemical Synthesis and Purification of Ser-Rev4

Synthesis of a non-C-terminal amide analog of Rev4 in which an extra Ser was added to the N-terminus (Ser Arg Arg Trp Pro Trp Trp Pro Trp Lys Trp Pro Leu Ile) (SEQ ID NO:5) was contracted with Genosys Biotechnologies Inc. HPLC analysis using a VYDAC reverse phase C8 column eluted with a 10–90% gradient of acetonitrile over 34 minutes at a flow rate of 1.5 ml per minute showed the peptide to be greater than 95% pure with a single peak eluting after 22.363 minutes.

EXAMPLE 4

Chemical Synthesis and Purification of Rev4-C-Terminal Fusion Peptide

Synthesis of a Rev4 with a C-terminal extension of 13 amino acids (Arg Arg Trp Pro Trp Trp Pro Trp Lys Trp Pro Leu Ile Gly Gly Gly Tyr Asp Pro Ala Pro Pro Pro Pro Pro) (SEQ ID NO:6) was contracted with Genosys Biotechnologies Inc. HPLC analysis using a VYDAC reverse phase C8 column eluted with a 10–90% gradient of acetonitrile over 34 minutes at a flow rate of 1.5 ml per minute showed the peptide to be greater than 95% pure with a single peak eluting after 21.213 minutes.

EXAMPLE 5

Chemical Synthesis and Purification of Indolicidin F (Amide)

Synthesis of a C-amidated indolicidin in which the Trp residues were replaced with Phe (Ile Leu Pro Phe Lys Phe Pro Phe Phe Pro Phe Arg Arg) (SEQ ID NO:7) was contracted with Genosys Biotechnologies Inc. HPLC analysis using a VYDAC reverse phase C8 column eluted with a 10–90% gradient of acetonitrile over 34 minutes at a flow rate of 1.5 ml per minute showed the peptide to be greater than 95% pure with a single peak eluting after 20.415 minutes.

EXAMPLE 6

Chemical Synthesis and Purification of Indolicidin F-P (Amide)

Synthesis of a C-amidated derivative of indolicidin in which the Trp residues were replaced by Phe and a Pro residue was deleted (Ile Leu Lys Gly Phe Pro Gly Phe Pro Arg Arg Lys) (SEQ ID NO:8) was contracted with Genosys Biotechnologies Inc. HPLC analysis using a VYDAC reverse phase C8 column eluted with a 10–90% gradient of acetonitrile over 34 minutes at a flow rate of 1.5 ml per minute showed the peptide to be greater than 95% pure with a single peak eluting after 15.527 minutes.

EXAMPLE 7

Stability of Reverse Peptides to Proteases Present in Plant Extracellular Fluid (ECF)

The stability of various reverse peptide versions of naturally occurring peptides was determined by incubating the reverse peptides with various dilutions of ECF and then measuring by HPLC analysis the percentage of parent peptide remaining at the end of the incubation period. See FIG. 2. ECF was obtained from tobacco leaves in accordance with the method described in U.S. Pat. No. 5,424,395. Fifty micrograms of each peptide was incubated with different amounts of ECF in 50 mM Tris-HCl buffer, pH 7.5, total volume 50 microliters, for one hour at 37° C. The reaction was stopped by adding 1% trifluoroacetic acid (TFA). A sample of the reaction mixture (20 μL) was injected onto a Vydac C4 column (4.6×250 mm) in a Waters HPLC system with 515 pumps, 486 detector and Millennium software. The sample was eluted with a gradient of 0.1% TFA in water to 60% acetonitrile in 0.1% TFA. The area of the peak corresponding to the undigested peptide was integrated and compared with the equivalent peak from a 0% ECF control. The non-reverse peptide, MYP30 (Met Gly Ile Gly Lys Phe Leu Arg Glu Ala Gly Lys Phe Gly Lys Ala Phe Val Gly Glu Ile Met Lys Pro) (SEQ ID NO:1), was included as a reference. The ranking of peptide stabilities shown in FIG. 2 was Rev4 (reverse indolicidin; Arg Arg Trp Pro Trp Trp Pro Trp Lys Trp Pro Leu Ile)(SEQ ID NO:4) >Rev6 (reverse PGLc; Leu Ala Lys Leu Ala Val Lys Ala Ile Lys Gly Ala Ile Ala Gly Ala Lys Ser Ala Met Gly) (SEQ ID NO:9)>Rev3 (reverse cecropin P1; Arg Pro Gly Gly Gln Ile Ala Ile Ala Ile Gly Glu Ser Ile Arg Lys Lys Ala Ser Asn Glu Leu Lys Lys Ala Thr Lys Ser Leu Trp Ser)(SEQ ID NO:10) >MYP30 (Met Gly Ile Gly Lys Phe Leu Arg Glu Ala Gly Lys Phe Gly Lys Ala Phe Val Gly Glu Ile Met Lys Pro) (SEQ ID NO:1) >Rev2 (reverse cecropin amide; Lys Ala Ile Gln Thr Ala Gln Gly Val Val Ala Val Ala Pro Gly Ala Lys Ile Ile Gly Asp Arg Ile Asn Gln Gly Val Lys Glu Ile Lys Lys Phe Leu Lys Trp Lys) (SEQ ID NO:11) >Rev8 (reverse bobinin-like peptide; Asn Ala Phe His Glu Ala Leu Gly Lys Ala Leu Gly Lys Leu Ala Ser Lys Gly Ala Ser Leu Ile Ser Ala Gly Ile Gly)(SEQ ID NO:12).

EXAMPLE 8

Stability of Rev4 to Proteases Present in Whole Cell Extract (WCE)

Whole cell extract (WCE) was prepared by grinding one gram of Kentucky 14 tobacco leaf tissue in liquid nitrogen, followed by extraction with 3 mL of 100 mM Tris-HCl buffer, pH 7.5, 50 mM NaCl. The mixture was clarified by spinning in a microcentrifuge (14,000 r.p.m., 5 minutes). The supernatant (WCE) was kept frozen as aliquots at −80° C. until required for an assay. Fifty micrograms of each peptide was incubated with different amounts of WCE in 50 mM Tris-HCl buffer, pH 7.5, total volume 50 microliters, for one hour at 37° C. The reaction was stopped by adding 1% trifluoroacetic acid (TFA). A sample of the reaction mixture (20 µL) was injected onto a Vydac C4 column (4.6×250 mm) in a Waters HPLC system with 515 pumps, 486 detector and Millenium software. The sample was eluted with a gradient of 0.1% TFA in water to 60% acetonitrile in 0.1% TFA. The area of the peak corresponding to the undigested peptide was integrated and compared with the equivalent peak from a 0% WCE control. MYP 30 (Met Gly Ile Gly Lys Phe Leu Arg Glu Ala Gly Lys Phe Gly Lys Ala Phe Val Gly Glu Ile Met Lys Pro) (SEQ ID NO:1) is more susceptible to degradation by WCE than ECF, but Rev4 (Arg Arg Trp Pro Trp Trp Pro Trp Lys Trp Pro Leu Ile) (SEQ ID NO:4) is much more stable to WCE than either MYP30 or Magainin 2 (Gly Ile Gly Lys Phe Leu His Ser Ala Lys Lys Phe Gly Lys Ala Phe Val Gly Glu Ile Met Asn Ser)(SEQ ID NO:13).

EXAMPLE 9

Ability of Rev4 to Protect Magainin 2 from Degradation by WCE

Assays for WCE protease degradation were performed as described in Example 8 except that one of the samples represented Magainin 2 that was mixed with Rev4 before the addition of WCE. The amounts of Magainin 2 and Rev4 remaining in the mixture were determined by HPLC as described for Examples 7 and 8. Rev4 was able to confer on Magainin 2 a stability to WCE equal to that of Rev4 itself (Table 2).

| | % Peptide Remaining Intact after 1 Hr. | | | |
|---|---|---|---|---|
| % WCE | Magainin 2 | Rev 4 | Magainin 2 in Rev4 + Magainin 2 Mix | Rev4 in Magainin 2 + Rev4 Mix |
| 0 | 100 | 100 | 100 | 100 |
| 15 | 10.9 | 82.7 | 89.7 | 89.6 |
| 30 | 0.3 | 77.2 | 87.6 | 84.0 |
| 45 | 0.4 | 66.9 | ND | ND |
| 60 | 0.3 | 61.6 | 73.1 | 75.3 |
| 90 | 0.4 | 55.2 | 56.3 | 53.8 |

ND = not determined

EXAMPLE 10

Ability of Rev4 to Protect Proteins from Degradation by Commercial Protease

The ability of Rev4 to inhibit four different classes of proteases was tested using fluorescent labeled casein as substrate under the following conditions:

| Enzyme | Class | Enzyme Concentration (mg/mL) | Assay Buffer |
|---|---|---|---|
| Chymotrypsin | Serine Protease | 0.01 | 5 mM Tris-HCl, pH8.0 |
| Carboxypeptidase | Zinc Metalloprotease | 0.10 | 5 mM Tris-HCl, pH8.0 |
| Papain | Sulfhydryl Protease | 0.01 | 5 mM MES, pH6.2 |
| Pepsin | Acid Protease | 0.01 | 5 mM HCl, pH2.0 |

Each protease was incubated with substrate (5 µg/mL fluorescent labeled casein; Molecular Probes Inc., Eugene, Oreg.) and peptide in a total volume of 200 µL in a 96-well microtiter plate. Before use, papain was activated with cysteine (Arnon, 1970, Methods in Enzymology 19:226–44). After incubation at room temperature for one hour, fluorescence due to casein digestion was measured in a Luminescence Spectrometer (LS50B, Perkin Elmer Ltd., England) with an excitation wavelength of 505 nm and an emission wavelength of 513 nm. The blank control contained the substrate, buffer and peptide but lacked the protease. Under these conditions, Rev4 was found to inhibit chymotrypsin, carboxypeptidase and papain, but not pepsin (Table 3).

| Protease | % Inhibition of Proteolysis by Rev4 at Various Concentrations (µg/ml) | | | | | | | |
|---|---|---|---|---|---|---|---|---|
| | 0 | 2.5 | 5 | 10 | 20 | 25 | 50 | 100 |
| Chymotrypsin | 0 | 16 | 42 | 75 | 97 | | | |
| Carboxypeptidase | 0 | 58 | 92 | 100 | 100 | | | |
| Papain | 0 | 29 | 72 | 93 | 99 | | | |
| Pepsin | 0 | | | | | 3 | 0 | 0 |

EXAMPLE 11

Antifungal Activity of Rev4

When subjected to blind testing by two independent research groups, Rev4 was identified to have broad spectrum activity against important plant pathogens including *Cercospora* spp., *Colletotrichum* spp., *Fusarium* spp. and *Helminthosporium* spp.

Tobacco blue mold (*Peronospora tabacina*) was used to compare the antifungal activity of Rev4 with that of MYP30. Spores of *Peronospora tabacina* were harvested from infected tobacco leaf with sterile water and washed three times. The spore suspension was diluted to 2,000 spores per mL. Peptide solution (2 µL) was added to spore suspension (48 µL) in a 96-well microtiter plate. After incubation in the dark at room temperature for 24 hours, the number of germinated spores was determined microscopically. Rev4 was found to be significantly more potent than MYP30.

| Peptide | Concentration (μg/mL) | Spore Germination (%) |
|---------|----------------------|----------------------|
| MYP30   | 0                    | 71                   |
|         | 1                    | 60                   |
|         | 5                    | 28                   |
|         | 25                   | 10                   |
|         | 50                   | 0                    |
| Rev4    | 0                    | 71                   |
|         | 1                    | 46                   |
|         | 5                    | 2                    |
|         | 25                   | 0                    |
|         | 50                   | 0                    |

The antifungal activity of Rev4 and related peptides was also compared using two tomato pathogens, *Verticillium dahliae* racel and *Alternaria alternata* f.sp. *lycopersici*. Spores were harvested from pure cultures grown on V8 medium, diluted to 5,000 spores per mL, and tested against dilution series of peptides in 96-well plates as described in U.S. Pat. No. 5,424,395. The minimum concentration required to completely inhibit spore germination for at least 48 hours was determined in triplicate:

EXAMPLE 12

| Peptide SEQ. ID No. | *Verticillium dahliae* | *Alternaria alternata* |
|---------------------|------------------------|------------------------|
| SEQ. ID No. 4       | 40 μg/ml               | 50 μg/ml               |
| SEQ. ID No. 5       | 50 μg/ml               | 100 μg/ml              |
| SEQ. ID No. 6       | 23 μg/ml               | 50 μg/ml               |
| SEQ. ID No. 7       | 50 μg/ml               | 100 μg/ml              |

EXAMPLE 12

Antifungal Activity of Rev4-Related Peptides

The peptides described as SEQ. ID Nos. 4, 5, 6, 7 and 8 in Examples 1, 3, 4, 5 and 6 were tested for antifungal activity as described in Example 11. All the Rev-related peptides showed significant inhibition of *Peronospora tabacina* spore germination when tested at a final concentration of 2 μg/mL.

EXAMPLE 13

| Peptide Treatment | % Germination (mean +/- sem) | % Control |
|-------------------|------------------------------|-----------|
| None (control)    | 76.6 +/- 11.2                | 100       |
| SEQ. ID NO. 4 (Rev4) | 3.7 +/- 3.2               | 4         |
| SEQ. ID NO. 5     | 6.8 +/- 6.3                  | 9         |
| SEQ. ID NO. 6     | 5.7 +/- 9.8                  | 7         |
| SEQ. ID NO. 7     | 8.8 +/- 5.4                  | 11        |
| SEQ. ID NO. 8     | 17.3 +/- 3.5                 | 23        |

EXAMPLE 13

Ability of Rev4-Related Peptides to Protect a Protein Against Chymotrypsin

The peptides described in EXAMPLE 12 were tested for their effects on the action of chymotrypsin on casein using the methods described in EXAMPLE 10. Peptides related to Rev4 but comprising amino acid extensions on either the N-terminus (Ser Arg Arg Trp Pro Trp Trp Pro Trp Lys Trp Pro Leu Ile) (SEQ ID NO:5) or C-terminus (Arg Arg Trp Pro Trp Trp Pro Trp Lys Trp Pro Leu Ile Gly Gly Gly Tyr Asp Pro Ala Pro Pro Pro Pro Pro Pro) (SEQ ID NO:6) protected fluorescent-labeled casein from the action of chymotrypsin. Peptides related to indolicidin (Ile Leu Pro Trp Lys Trp Pro Trp Trp Pro Trp Arg Arg) (SEQ ID NO:2) in which Trp residues were replaced by Phe (Ile Leu Pro Phe Lys Phe Pro Phe Phe Pro Phe Arg Arg(SEQ ID NO:7); Ile Leu Lys Gly Phe Pro Gly Phe Pro Arg Arg Lys)(SEQ ID NO:8) did not have this protective effect, even though they had retained antifungal activity (EXAMPLE 12).

EXAMPLE 14

| Peptide Identity | Peptide Concentration (μg/mL) | Chymotrypsin Activity (Fluorescence Units) Mean | +/- s.e.m. |
|------------------|-------------------------------|-------------------------------------------------|------------|
| None (control)   | 0                             | 375                                             | 58         |
| SEQ. ID NO. 5    | 5                             | 162                                             | 25         |
| SEQ. ID NO. 5    | 20                            | 44                                              | 18         |
| SEQ. ID NO. 6    | 5                             | 212                                             | 22         |
| SEQ. ID NO. 6    | 20                            | 45                                              | 6          |
| SEQ. ID NO. 7    | 5                             | 386                                             | 71         |
| SEQ. ID NO. 7    | 20                            | 385                                             | 13         |
| SEQ. ID NO. 8    | 5                             | 385                                             | 85         |
| SEQ. ID NO. 8    | 20                            | 321                                             | 68         |

Construction of a Gene ("RIL") Encoding Rev4 Peptide

A DNA sequence encoding Rev4 (Arg Arg Trp Pro Trp Trp Pro Trp Lys Trp Pro Leu Ile (SEQ ID NO:14), no C-terminal amide) was designed according to the standard genetic codon and the tobacco codon usage table (found at web site http://www.dna.affrc.go.jp). Two oligonucleotide primers (AGGAGATGGCCTTGGTGGCCTTG-GAAATGGCCTCTTATT (SEQ ID NO:15) and CCAGTCTCTAGAACCATGAGGAGATGGCCTTGG) (SEQ ID NO:16) were used to make the full coding sequence to clone into expression vectors. Full-length DNA was generated by polymerase chain reaction (PCR: Sambrook et al., 1989, Molecular Cloning, A Laboratory Manual. Cold Spring Harbor Laboratory Press.). Taq DNA polymerase was purchased from Gibco BRL, and the reaction set up as suggested by the manufacturer. No template was needed for the PCR reaction because the two primers have overlapping regions (15 nucleotides). To facilitate the gene cloning, two restriction sites (XbaI and SacI) were engineered on both ends of the gene and extra nucleotides were added to the ends to ensure these enzyme digestions.

The digested PCR product was cloned into pbluescript II KS+ (or pBS, Stratagene, LaJolla, Calif.) plasmid vector with 5' AMV sequence in the multiple cloning site. The 5' AMV sequence, a translational enhancer from the 5' leader sequence of alfalfa mosaic virus (5' AMV; Jobling and Gehrke, 1987, Nature, 325:622–25), was used to enhance the translation of the mRNA. The RIL gene coding sequence was inserted into the vector behind this 5' AMV sequence (see FIG. 1). This construct, 5' AMV-RIL, was excised by digestion with XhoI and SacI and inserted into a binary vector pKLP36 (Maiti and Shepherd, 1998, Biochem. Biophys. Res. Comm. 244:440–44), yielding a construct named pKLP RIL. The pKLP36 vector contains the transfer DNA (T-DNA) right and left borders for gene insertion into plant genomes, a NPTII gene (for Kanamycin resistance) as a selectable marker for plant transformation, and the 36S promoter from peanut chlorotic streak caulimovirus and the 3' untranslated sequence from a Rubisco small subunit gene (rbcs3', FIG. 1) to drive the expression of the assembled RIL gene.

EXAMPLE 15

Assembly of a PreRIL Gene for Secretion of Rev4 in Plants

A secretion signal peptide sequence from tobacco PR-lb (Cornelissen et al., 1986, EMBO J. 5:34–40) was added to RIL to facilitate secretion of Rev4 into the extracellular space of plant tissues where invading pathogens might be first encountered. Two primers (GACTGGAGCTCT-TAAATAAGAGGCCATTTCCAAGGCCAC-CAAGGCCATCTCCT (SEQ ID NO:17) and AGCTGG-GAATTCTAGGAGATGGCCTTGGTGGC) (SEQ ID NO:18) were designed to introduce the signal sequence and preserve the native cleavage site for processing.

The PCR product (67 base pairs) was precipitated and digested with EcoRI and XbaI, then cloned into the pBS plasmid vector already containing the 5' AMV and PR-lb sequences to yield plasmid pBS PreRIL. The sequence identity was confirmed by DNA sequencing. The cassette 5' AMV-PR-lb-RIL was then excised with XhoI and XbaI and inserted into pKLP36 to create pKLPPreRIL.

EXAMPLE 16

Assembly of a Pro-Peptide PPRIL Gene Encoding Rev4 Peptide

Natural peptide hormones are initially synthesized as large prepro-hormone precursors that are processed to form the smaller active peptides (Hook et al., 1994, FASEB J. 8:1269–78). Pro-sequences can facilitate the trans-membrane movement of peptides and prevent the release of active peptide until it is in the correct cellular compartment. In this example we used a pro-sequence based on that found in natural magainin genes (Zasloff, 1987, PNAS 84:5449–53; ATGGACTCTAGATTAAATAAGAGGC-CATTTCCAAGGCCACCAAGGCCATCTCCT) (SEQ ID NO:19) and linked it to Rev4-coding sequence through a His-Ser motif that corresponds to the site at which plant extracellular proteases cleave natural magainins (Everett, 1994, Chpt. 20 In: Natural and Engineered Pest Management Agents, eds. Hedin, Menn & Hollingworth, ACS Symposium Series 551, pp. 278–91). Correct processing at this site should leave an additional Ser residue on the N-terminus of Rev4, a modification that has been shown not to significantly reduce biological activity (Examples 12 and 13). Two oligonucleotide primers (AGCTGGGAAT-TCTAGGAGATGGCCTTGGTGGC (SEQ ID NO:18) and nucleic acid sequence corresponding to Leu-Pro-Gln-Pro-Glu-Ala-Ser-Ala-Asp-Glu-Gly-Val-Asp-Glu-Arg-Glu-Leu-His$^x$-Ser (SEQ ID NO20) were used to generate the full-length gene by PCR as described above in previous Examples.

The PCR product was cloned into the pBS plasmid vector as in Example 15 to yield pBS PPRIL. As before, the gene cassette (5' AMV-PR-lb-Pro-RIL) was then inserted into pKLP36 as a XhoI/XbaI fragment and named pKLP PPRIL.

EXAMPLE 17

Assembly of PCRIL Gene Encoding Rev4 as a Fusion to a Fragment of PR-lb

The unusual amino acid composition and structure of Rev4 and related peptides might interfere with correct peptide secretion or processing if the Rev4 sequence is directly adjacent to the natural signal peptide processing site. This would be similar to the importance of both the transit peptide and the transported protein sequence for protein transport into chloroplasts (Wassman et al., 1986, Mol. Gen. Genet., 205:446–53). Accordingly, PCRIL was designed so that the Rev4 peptide would be fused to the C-terminus of a peptide corresponding to the first 20 amino acids of the PR-lb coding sequence, which naturally follows the PR-lb signal sequence. To facilitate release of Rev4 peptide from the PR-lb-Rev4 fusion product, the junction between PR-lb and Rev4 was engineered to include a cleavage site (Ala-Ala-Lys-Ile-) (SEQ ID NO:27) that would be recognized by pepsin-like acid proteases that should not be inhibited by Rev4 (Example 10) and are produced by many fungi (Shintani et al., 1997, J. Biol. Chem. 272: 18855–61, Morihara and Oka, 1973, Arch. Biochem. Biophys., 157:561–72).

The DNA encoding PR-lb signal peptide and the first 20 amino acids of the mature PR-lb protein was cloned by PCR from genomic DNA of Nicotiana tabacum cv Samsun NN using two oligonucleotide primers (AGCACTGAAT-TCTCTTCCACAACCAGA GGCTTCTGCTGATGAAG-GTGTTGATGAAAGAGAGCTCCATTCTAG-GAGATGGCCTTGGTGG (SEQ ID NO:21) and GTCACCTGCAGCCACGCCTACATCTGCAC) (SEQ ID NO:22). To be compatible with the cloning of the PR-lb protein coding sequence, the 5' cloning site of RIL was changed by a PCR reaction using CCAGTCTCTAGAAC-CATGAGGAGATGGCCTTGG (SEQ ID NO:16) and a new primer, ACGAAGCTTACCATGGGATTTTTTCTC (SEQ ID NO:23). The cloned sequences were verified by DNA sequencing. The DNA and amino acid sequences of this construct are listed in AGTCACTGCAGCTAAGATTAG-GAGATGGCCTTGGTG (SEQ ID NO:24) and ATGG-GATTTTTTCTCTTTTCACAAATGCCCT-
CATTTTTTCTTGTCTCTACACTTCTCTTATT
CCTAATAATATCTCACTCTTCTCATGC-
CCAAAACTCTCAACAAGACTATTTGGATGCCCATA
ACACAGCTCGTGCAGATGTAGGCGTG-
GCTGCAGCTAAGATTAGGAGATGGCCT-
TGGTGGCCT TGGAAATGGCCTCTTATTTAA (SEQ ID NO:25), respectively. The gene cassette PCRIL as shown in FIG. 1 was first assembled in pBS and then moved into pKLP36, as described in previous Examples.

The resulting new plasmid was pKLP PCRIL.

EXAMPLE 18

Assembly of pPZP AMY and pPZP APM

In order to test the protective activity of the Rev4 peptide on Myp30 in vivo, we have cloned the Myp30 gene into a second binary vector pPZP (Hajdukiewicz et al., 1994, Plant Molecular Biology, 25:989–94) which contains the resistance gene of gentamycin as plant selection marker. This allows us to do a double transformation on the Rev4 containing plants with Myp30 gene as the second transformants can be selected as gentamycin resistance plants.

Myp30 (AMY) and PR-lb-Myp30 (APM) genes were excised as XhoI and SacI fragment from the pBS-AMY and pBS-APM constructs (Li et al., 1999, submitted for publication) and ligated to promoter EMV-FLt-10 in the context of pKYLX (Maiti et al., 1997, Transgenic Research, 6:143–56). Then the promoter, AMY or APM with rbcS 3' UTR sequences were excised out by an EcoRI and ClaI (blunted), and ligated to pPZP221 vector (prepared as EcoRI and SmaI cutting), and the resulting plasmids named as pPZP-AMY and pPZP-APM, respectively.

EXAMPLE 19

Production of Polyclonal Antibodies against Rev4

The synthetic Rev4 peptide from Example 1 was conjugated with keyhole limpet hemocyanin (Calbiochem, Inc.) following the procedure of Deen et al. (1990, J. Immunol. Methods 129:119–25). The conjugated and non-conjugated peptides were both injected into New Zealand rabbits as described by Ausubel et al. (1987, Current Protocols in Molecular Biology. Wiley Interscience Press.) After four sets of injections, the sera were collected, 0.01% sodium azide was added, and the sera was stored at −80° C.

EXAMPLE 20

Production of Transgenic Plants Expressing Rev4 Gene Constructs

The research described herein has identified a class of peptides, and their corresponding DNA sequences, that have enhanced stability against plant proteases and which may also stabilize other peptides, polypeptides or proteins against degradation by proteases of plant, fungal, insect or other origins. Agronomic, horticultural, ornamental, and other economically or commercially useful plants can benefit from this invention by introducing these DNAs therein in a functionally operable manner so that they are expressed at a level effective to confer on such transgenic plants improved disease resistance or some other improvement that is conferred by the expression of a peptide related to Rev4.

Because an important use of the invention is to use the introduction of a first gene encoding a Rev4-related peptide to protect the peptide, polypeptide or protein product of a second gene against protease degradation, the second gene may already be present in the plant to be transformed; or the first and second genes may be combined in one plant by sexual hybridization of two independent transformed plants, one containing the first gene and the other containing the second gene; or the two genes may be introduced simultaneously. Furthermore, instead of the gene products of the first and second gene being produced from different transcriptional units that are provided with separate promoters and other gene expression components, the two peptides, polypeptides, or proteins may be produced from a single transcriptional unit under the control of a single promoter. Such single transcriptional unit may represent a dicistronic unit in which the first and second gene sequences are separated by a DNA sequence which allows reinitiation of translation, or it may represent a single translational unit that produces a protein fusion product that comprises the peptide, polypeptide or protein product of the first gene fused to the peptide, polypeptide or protein product of the second gene. Such fusion product may either retain the activity and function of the individual products of the first and second gene, or the two individual products may be released from the fusion by a subsequent cleavage.

Transgenic plants that express biologically effective amounts of Rev4 and biologically functional equivalents thereof can be produced by:

(a) transforming plant cells with a recombinant DNA molecule comprising operatively linked in sequence in the 5' to 3' direction:

(i) a promoter region that directs the transcription of a gene in plants, (ii) an optional DNA sequence which encodes a signal sequence that directs the sorting of proteins in the secretory system (see for example Chrispeels, 1991, Ann. Rev. Plant Physiol. Plant Mol. Biol. 42:21–53)

(iii) a DNA coding sequence that encodes an RNA sequence which comprises a sequence which encodes Rev4 having essentially the same or similar biological properties as that of Rev4;

(iv) an optional DNA sequence which encodes a signal sequence that directs the sorting of proteins in the secretory system (see for example Chrispeels, 1991, Ann. Rev. Plant Physiol. Plant Mol. Biol. 42:21–53)

(v) a 3' non-translated region that encodes a polyadenylation signal which functions in plant cells to cause transcriptional termination and the addition of polyadenylate nucleotides to the 3' end of said RNA sequence;

(b) selecting plant cells that have been transformed (c) regenerating plant cells that have been transformed to produce differentiated, fertile, transgenic plants (d) selecting a transformed plant, cells of which express said DNA coding sequence and produce a biologically functionally equivalent thereof.

Methods for transforming a wide variety of dicotyledonous and monocotyledonous plants are well documented in the literature (see for example U.S. Pat. No. 5,773,696 and references therein). Such methods can be used by one ordinarily skilled in the art to produce transgenic plants that express biologically effective amounts of a Rev4-related peptide or biologically functionally equivalent thereof.

By way of a non-limiting example, the introduction into tobacco of gene constructs which encode Rev4-related peptides is described. To enable the use of *Agrobacterium*-mediated transformation, the pKLP constructs described in Examples 14, 15, 16, and 17 were transferred from *E. coli* to *Agrobacterium tumefaciens* C58. by a triparental mating procedure as described by Ditta et al. (1980, PNAS 77:7347–51).

The *Agrobacterium* containing RIL constructs were then used to transform tobacco (*Nicotiana tabacum* cv KY14) as described by Horsch et al. (1986, PNAS, 83:2571–75). Briefly, sterile leaf discs were co-cultured with the Agrobacteria on a non-selective medium (MS agar medium containing 3% sucrose and 2.5 mg/L benzylaminopurine, and 1 mg/L indole-3-acetic acid) for 2 days, followed by continued culture (transferred to fresh medium once a week) on selection medium (same as non-selective one but containing 300 mg/L kanamycin (Sigma, St. Louis) and 500 mg/L mefoxin (Merck and Co., West Point, Pa.). When the regenerated, kanamycin-resistant plants were at the 3–4 leaf stage, they were transferred to rooting medium (MS agar medium containing 3% sucrose and 500 mg/L mefoxin) for root induction. Plantllets with roots were transplanted to soil and grown to maturity in a standard greenhouse.

The same set of Agrobacteria was used to transform *Arabidopsis thaliana* ecotype Columbia by a vacuum infiltration protocol (Bent et al., 1994, Science 265:1856–60). Briefly, flowering *Arabidopsis* plants were dipped into the Agrobacteria suspension, then vacuum was applied for 3 minutes. The seeds from the treated plants were harvested and screened on appropriate selection markers (kanamycin or gentamycin both in 50 mg/l). Double transformation of pKLP and pPZP constructs in *Arabidopsis* were generated by transforming pPZP containing Agrobacteria to already transformed pKLP RIL, PCRIL PPRIL and PrcRIL *Arabidopsis* plants.

EXAMPLE 21

Detection of Rev4 mRNA in Transgenic Plants

Because the level of expression of a transgene can vary considerably between different transformation events, it is useful to categorize transformants into high, medium, or low expressors in preparation for further analysis. Total RNA was isolated from the leaves of 7 to 8 week old transgenic plants using the RNAqueous phenol-free total RNA isolation kit (Ambion Inc., Austin, Tex.). Equal amounts of total RNA (10 μg) from individual transformants were separated on a 1.2% agarose gel, transferred to Nytran (Schleicher & Schell, Keene, N.H.), hybridized with a $^{32}$P-labeled RIL DNA probe, and washed using standard protocols (Sambrook et al., 1989, Molecular Cloning, a Laboratory Manual. Cold Spring Harbor Laboratory Press.). The blots (not shown) were visualized by autoradiography and phospher imager (Fujifilm Fluorescent Image Analyzer FLA-2000, Fuji, Japan).

EXAMPLE 22

Detection of Increased Bacterial Pathogen Resistance in Transgenic Plants

Leaf tissue (300 mg) was collected from leaves of young plants (4–6 leaf stage) and homogenized in 200 μL of 2×SDS-PAGE sample buffer (0.125 M Tris HCl, pH 6.8, 20% [v/v] glycerol, 2% [w/v] SDS, 10% [v/v] beta-mercaptoethanol, and 0.001% [w/v] bromophenol blue) using a mortar and pestle. The samples were boiled for 10 minutes, centrifuged to pellet cell debris, and the supernatant stored at −20° C. for future analysis.

For immunoblot analysis, the proteins from 30 mg of leaf tissue were separated by 16.5% Tris-Tricine SDS-PAGE (Schagger and Jagow, 1987, Anal. Biochem. 166:368–79, precast gels from Bio-Rad Laboratories) and transferred to a nitrocellulose membrane using a Trans Blot Cell (Bio-Rad Laboratories) following the manufacturer's recommendations. Filters were probed with polyclonal antibodies specific for the Rev4 peptide (Example 18). Briefly, filters containing transferred proteins were incubated at room temperature in TTBS (20 mM Tris-HCl, pH 7.5, 0.5 M NaCl, 0.05% [v/v] Tween 20, 3% [w/v] nonfat dried milk) for 30 minutes, followed by incubation with the Rev-4 specific antibodies for 1 hour in the same buffer. After the excess antibodies were removed with four washes (5 minutes each) of TTBS, the filters were incubated for 30 minutes with 3% milk-TTBS containing peroxidase-conjugated goat antirabbit IgG (Jackson Immuno Research Laboratories, Inc., West Grove, Pa.). The excess second antibody was removed with four washes of TTBS and two washes of water. Filters were then developed with Chemilumuniscence Reagent Plus Kit (DuPont NEN Research Products, Boston, Mass.), and the resulting chemiluminescence detected by exposure to photographic film.

The expression of RIL genes in transgenic plants can also be detected using phenotypic analyses such as increased disease resistance or any other convenient phenotype that results from the biological properties of Rev4-related peptides in combination with a second biologically active peptide, polypeptide or protein.

EXAMPLE 23

Detection of Increased Bacterial Pathogen Resistance in Transgenic Plants

Increases in bacterial disease resistance can be performed in progeny of the primary transformants. A tobacco bacterial pathogen, Erwinia carotovora subsp. carotovora (Pirhonen et al., 1991, Molecular Plant-Microbe interactions, 4:276–83) was used for the testing of tobacco plants. The overnight culture of the bacteria was centrifuged (1,000×g) and the pellet resuspended in sterile water until a solution with an $OD_{600}$-0.8 was obtained. Two μl of the bacterial suspension were dropped onto an extended leaf of individual tobacco seedlings (5–6 weeks old) grown in a 24-well microtiter plate in MS medium. The tobacco seedlings were cultured in a growth chamber 23–24° C., with 10 hours light/14 hours dark period. Individual experiments consisted of 8 plants per replication and at least 6 replications for each transgenic line. After 14 days, the number of dead plants was recorded.

| Plant Line Code | % Plants Surviving Erwinia carotovora Test |
|---|---|
| KYLX (Control) | 16 |
| RIL 26 | 48 |
| PCRIL 24 | 36 |
| PCRIL 26 | 61 |

Table Erwinia carotovora resistance tests of Rev4 transgenic tobacco plants. Two μl of a bacterial suspension were inoculated onto the leaf of each tobacco seedling (4 weeks old), cultured in 24-well plates containing MS medium. Each test involved 8 replications of 6 plants for each transgenic line and the KYLX control.

For testing bacterial resistance of Rev4 transformed Arabidopsis, Pseudomonas syringae pv. maculicola ES4326 was used. An overnight culture of the bacteria was spun down and resuspended in 10 mM MgSO4 with Silwet 1-77 (200 μl/liter), to make OD600–0.001. Four week-old Arabidopsis plants (grown at 8 hours light/16 hours dark, 23° C.) were dipped in the bacterial solution, briefly drained and returned to the growth chamber. After 4 days, pictures were taken and the average infected leaves in each group were grounded and spread on LB medium for bacteria counting.

EXAMPLE 24

Detection of Increased Fungal Pathogen Resistance in Transgenic Plants

Tobacco blue mold (Peronospora tabacina) was used to test transgenic tobacco plants for increased disease resistance to this fungal pathogen. Tobacco leaf panels (8 panels per leaf, one leaf per plant of the same age, and three plants of each line) were infiltrated with 100 spores in water solution (10 μL). After 7 days, the total infected area on the individual leaves was measured. The reduction of the disease severity was calculated as percentage of that seen with a water control.

For the fungal resistance of Arabidopsis Rev4 transgenic plants, Peronospora parasitica var. Noco 2 was used to the testing. The active spores of the fungus (in water, 50,000 spores/ml) was sprayed on the 2 week-old Arabidopsis seedlings. After 6 days, the symptoms were recorded by photograph. The growth condition of the *Arabidopsis* plants were the same as in Example 22.

| PLANT LINE | AVERAGE NO. SPORES × $10^3/cm^2$ | STANDARD DEVIATION |
|---|---|---|
| KIX (control) | 274 | 77 |
| ril 24 | 169 | 43 |
| pcril 24 | 169 | 65 |
| pcril 26 | 135 | 31 |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A peptide comprising Rev$^4$(Arg-Arg-Trp-Pro-Trp-Trp-Pro-Trp-Lys-Trp-Pro-Leu-Ile) (SEQ ID NO: 4) or a functional equivalent thereof with the same sequence, but for conservative amino acid substitutions.

2. A composition for use in protecting a peptide, polypeptide or protein from protease degradation, comnrising Rev4 or a functional equivalent thereof and a carrier,
   wherein said functional equivalent comprises the formula: X-X-Y-Y-Y-Y-Y-Y-X-Y-Y-Y-Y wherein each X is independently arginine, lysine or histidine; and wherein each Y is independently tryptophan, glycine, alanine, valine, leucine, isoleucine, proline, phenylalanine, methionine, or lysine.

3. The composition of claim 2 further comprising a protein selected from the group consisting of proteins derived from *Bacillus thuringiensis* (B.t.), other *Bacillus* species, or *Photorhabdus* or *Xenorhabdus* species; proteins involved in improving the quality of plant products or agronomic performance of plants; peptides or proteins produced in plants for the purpose of extraction and use as pharmaceutical products, agricultural products, feed or food additives; industrial enzymes; peptides or proteins that cause an alteration in plant metabolism that leads to the production of metabolites that can be extracted and used as pharmaceutical products, feed and food additives; fungicides and insecticides.

* * * * *

SEQUENCE LISTING

<160> NUMBER OF SEQ ID NOS: 27

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 1

Met Gly Ile Gly Lys Phe Leu Arg Glu Ala Gly Lys Phe Gly Lys Ala
 1               5                  10                  15

Phe Val Gly Glu Ile Met Lys Pro
            20

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 2

Ile Leu Pro Trp Lys Trp Pro Trp Trp Pro Trp Arg Arg
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 3

Ile Leu Lys Lys Trp Pro Trp Trp Pro Trp Arg Arg Lys
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 4

Arg Arg Trp Pro Trp Trp Pro Trp Lys Trp Pro Leu Ile
 1               5                  10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 5

Ser Arg Arg Trp Pro Trp Trp Pro Trp Lys Trp Pro Leu Ile
 1               5                  10

<210> SEQ ID NO 6
<211> LENGTH: 26
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 6

Arg Arg Trp Pro Trp Trp Pro Trp Lys Trp Pro Leu Ile Gly Gly Gly
 1               5                  10                  15

Tyr Asp Pro Ala Pro Pro Pro Pro Pro Pro
            20                  25

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 7

Ile Leu Pro Phe Lys Phe Pro Phe Phe Pro Phe Arg Arg
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 8

Ile Leu Lys Gly Phe Pro Gly Phe Pro Arg Arg Lys
 1               5                  10

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 9

Leu Ala Lys Leu Ala Val Lys Ala Ile Lys Gly Ala Ile Ala Gly Ala
 1               5                  10                  15

Lys Ser Ala Met Gly
            20

<210> SEQ ID NO 10
<211> LENGTH: 31

```
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 10

Arg Pro Gly Gly Gln Ile Ala Ile Ala Ile Gly Glu Ser Ile Arg Lys
 1               5                  10                  15

Lys Ala Ser Asn Glu Leu Lys Lys Ala Thr Lys Ser Leu Trp Ser
            20                  25                  30

<210> SEQ ID NO 11
<211> LENGTH: 37
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 11

Lys Ala Ile Gln Thr Ala Gln Gly Val Val Ala Val Ala Pro Gly Ala
 1               5                  10                  15

Lys Ile Ile Gly Asp Arg Ile Asn Gln Gly Val Lys Glu Ile Lys Lys
            20                  25                  30

Phe Leu Lys Trp Lys
        35

<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 12

Asn Ala Phe His Glu Ala Leu Gly Lys Ala Leu Gly Lys Leu Ala Ser
 1               5                  10                  15

Lys Gly Ala Ser Leu Ile Ser Ala Gly Ile Gly
            20                  25

<210> SEQ ID NO 13
<211> LENGTH: 23
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 13

Gly Ile Gly Lys Phe Leu His Ser Ala Lys Lys Phe Gly Lys Ala Phe
 1               5                  10                  15

Val Gly Glu Ile Met Asn Ser
            20

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 14
```

Arg Arg Trp Pro Trp Trp Pro Trp Lys Trp Pro Leu Ile
 1               5                  10

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
aggagatggc cttggtggcc ttggaaatgg cctcttatt                          39

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16
ccagtctcta gaaccatgag gagatggcct tgg                                33

<210> SEQ ID NO 17
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 17
gactggagct cttaaataag aggccatttc caaggccacc aaggccatct cct          53

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 18
agctgggaat tctaggagat ggccttggtg gc                                 32

<210> SEQ ID NO 19
<211> LENGTH: 54
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
atggactcta gattaaataa gaggccattt ccaaggccac caaggccatc tcct         54

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      antimicrobial peptide

<400> SEQUENCE: 20

Leu Pro Gln Pro Glu Ala Ser Ala Asp Glu Gly Val Asp Glu Arg Glu
 1               5                  10                  15

Leu His Ser

<210> SEQ ID NO 21
<211> LENGTH: 88
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
agcactgaat tctcttccac aaccagaggc ttctgctgat gaaggtgttg atgaaagaga      60
gctccattct aggagatggc cttggtgg                                         88

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
gtcacctgca gccacgccta catctgcac                                        29

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 23
acgaagctta ccatgggatt ttttctc                                          27

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 24
agtcactgca gctaagatta ggagatggcc ttggtg                                36

<210> SEQ ID NO 25
<211> LENGTH: 207
<212> TYPE: DNA
<213> ORGANISM: Artificial Sequence
<220> FEATURE:
<223> OTHER INFORMATION: Description of Artificial Sequence: DNA PCRIL
      construct

<400> SEQUENCE: 25
atgggatttt ttctcttttc acaaatgccc tcatttttc ttgtctctac acttctctta       60
ttcctaataa tatctcactc ttctcatgcc caaaactctc aacaagacta tttggatgcc     120
cataacacag ctcgtgcaga tgtaggcgtg gctgcagcta agattaggag atggccttgg     180
tggccttgga atggcctct tatttaa                                          207

<210> SEQ ID NO 26
<211> LENGTH: 68
<212> TYPE: PRT
<213> ORGANISM: Artificial Sequence

```
<220> FEATURE:
<223> OTHER INFORMATION: Description of Artificial Sequence: Amino acid
      PCRIL construct

<400> SEQUENCE: 26

Met Gly Phe Phe Leu Phe Ser Gln Met Pro Ser Phe Phe Leu Val Ser
 1               5                  10                  15

Thr Leu Leu Leu Phe Leu Ile Ile Ser His Ser Ser His Ala Gln Asn
             20                  25                  30

Ser Gln Gln Asp Tyr Leu Asp Ala His Asn Thr Ala Arg Ala Asp Val
         35                  40                  45

Gly Val Ala Ala Ala Lys Ile Arg Arg Trp Pro Trp Trp Pro Trp Lys
     50                  55                  60

Trp Pro Leu Ile
 65

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      cleavage site

<400> SEQUENCE: 27

Ala Ala Lys Ile
 1
```